United States Patent
Ilan et al.

(10) Patent No.: US 11,911,448 B2
(45) Date of Patent: Feb. 27, 2024

(54) STABLE LIQUID THROMBIN COMPOSITIONS

(71) Applicant: Omrix Biopharmaceuticals Ltd., Rehovot (IL)

(72) Inventors: Erez Ilan, Kibbutz Netzer Sereni (IL); Omri Faingold, Rehovot (IL); Sivan Doron, Moshav Arugot (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 86 days.

(21) Appl. No.: 16/535,398

(22) Filed: Aug. 8, 2019

(65) Prior Publication Data

US 2020/0054720 A1 Feb. 20, 2020

Related U.S. Application Data

(60) Provisional application No. 62/764,856, filed on Aug. 16, 2018.

(30) Foreign Application Priority Data

Aug. 16, 2018 (IL) .......................................... 261190

(51) Int. Cl.
| | | |
|---|---|---|
| A61K 47/10 | (2017.01) | |
| A61K 38/48 | (2006.01) | |
| A61K 47/02 | (2006.01) | |
| A61P 7/04 | (2006.01) | |
| A61K 47/42 | (2017.01) | |

(52) U.S. Cl.
CPC .......... *A61K 38/4833* (2013.01); *A61K 47/02* (2013.01); *A61K 47/10* (2013.01); *A61K 47/42* (2013.01); *A61P 7/04* (2018.01); *C12Y 304/21005* (2013.01)

(58) Field of Classification Search
CPC .... A61K 38/4833; A61K 47/10; A61K 47/02; A61K 47/42; A61K 9/08; C12Y 304/21005; A61P 7/04
See application file for complete search history.

(56) References Cited

U.S. PATENT DOCUMENTS

| | | | |
|---|---|---|---|
| 4,631,055 A | 12/1986 | Redl | |
| 4,696,812 A * | 9/1987 | Silbering | A61P 7/04 424/445 |
| 4,846,405 A | 7/1989 | Zimmermann | |
| 4,965,203 A * | 10/1990 | Silbering | A61K 47/02 424/94.64 |
| 5,116,315 A | 5/1992 | Capozzi et al. | |
| 5,582,596 A | 12/1996 | Fukunaga | |
| 5,665,067 A | 9/1997 | Linder | |
| 5,989,215 A | 11/1999 | Delmotte | |
| 6,121,232 A | 9/2000 | Nur et al. | |
| 6,461,361 B1 | 10/2002 | Epstein | |
| 6,585,696 B2 | 7/2003 | Petersen | |
| 6,620,125 B1 | 9/2003 | Redl | |
| 6,802,822 B1 | 10/2004 | Dodge | |
| 7,473,543 B2 * | 1/2009 | Jiang | A61L 24/106 435/7.1 |
| 2005/0037088 A1 | 2/2005 | Pendharkar et al. | |
| 2006/0270015 A1 | 11/2006 | Pawlak | |
| 2010/0183582 A1 | 7/2010 | Pendharkar et al. | |
| 2014/0120078 A1 | 5/2014 | Wallace | |
| 2015/0037314 A1 * | 2/2015 | Larsen | A61K 9/1658 424/94.64 |

FOREIGN PATENT DOCUMENTS

| | | |
|---|---|---|
| CN | 101365467 A | 2/2009 |
| CN | 102380100 A | 3/2012 |
| CN | 107427601 A | 12/2017 |
| EP | 0277096 A3 | 4/1989 |
| EP | 0534178 | 4/2001 |
| EP | 0993311 | 7/2010 |
| WO | 039212 A2 | 12/1996 |
| WO | 98/033533 | 8/1998 |
| WO | 07/059801 | 5/2007 |
| WO | WO2010095128 A3 | 10/2010 |

OTHER PUBLICATIONS

Ethicon. SurgiFlo hemostatic matrix kit. 2014;1-16.*
Macdonald, et al., An in vivo comparison of the efficacy of hemostatic powders, using two porcinebleeding models, Medical Devices: Evidence and Research, 2017, pp. 273-279, vol. 10.
Nagura, et al., Structures and Physical Properties of Cross-Linked Gelatin Fibers, Polymer Journal, Aug. 8, 2002, pp. 761-766, vol. 34 Issue 10.
Chinese Search Report, dated Jul. 1, 2022, pp. 1-3.
International Preliminary Report, PCT/IL2019/000002, dated Feb. 16, 2021, pp. 1-7.
Brazilian Preliminary Office Action, dated May 24, 2023, pp. 1-4.

* cited by examiner

*Primary Examiner* — Lynn Y Fan
(74) *Attorney, Agent, or Firm* — David R. Crichton

(57) ABSTRACT

The present invention provides methods for large scale preparation of sterile stable liquid thrombin composition comprised of glycerol; stable liquid thrombin compositions; and hemostatic composition and kits. The present invention further provides hemostatic compositions comprised of liquid thrombin, glycerol and gelatin. Further provided herein is a method for the large-scale production of a sterile liquid thrombin composition comprised of glycerol.

5 Claims, 3 Drawing Sheets

STABLE LIQUID THROMBIN COMPOSITIONS

CROSS-REFERENCE TO RELATED APPLICATIONS

This application claims the benefit of U.S. provisional application 62/764,856 filed Aug. 16, 2018, and IL application 261190 filed Aug. 16, 2018, the complete disclosures of which are hereby incorporated herein by reference for all purposes.

FIELD OF THE INVENTION

The present invention relates, inter alia, to stable liquid thrombin compositions comprising glycerol, their preparation, and hemostatic kits comprising thereof. The present invention further relates to sterile liquid thrombin compositions comprising glycerol.

BACKGROUND OF THE INVENTION

The control of bleeding is essential and critical, especially in surgical procedures, to minimize blood loss, to reduce post-surgical complications, and to shorten the duration of the surgery in the operating room. While hemostatic preparations comprising thrombin are available, the thrombin is either frozen or provided in a powder form, due to its autocatalytic function, which renders the thrombin unstable. Several preparations of liquid thrombin are currently known, for example:

European Patent No. EP0277096 discloses thrombin formulations rendered stable at room temperature using stabilizing quantities of a polyol and a buffer at a specific pH.

U.S. Pat. No. 4,696,812 discloses thrombin solutions rendered storage stable using stabilizing quantities of an anti-autolytic buffer in combination with low levels of saline and glycerol to prevent denaturation.

U.S. Pat. No. 4,965,203 discloses improved thrombin formulations, stable at room temperature using stabilizing quantities of a polyol and a buffer at a specific pH.

US Patent Application having Publication No. US20060270015 discloses stabilized, liquid formulations containing thrombin having a high degree of purity and a high specific activity and methods of making and using such formulations.

US Patent Application having Publication No. US20140120078 discloses cross-linked hydrogels and kits including them, which may additionally comprise a plasticizer (e.g., glycerol), and a bioactive agent such as thrombin.

SUMMARY OF THE INVENTION

Liquid thrombin preparations may be made into a lyophilized medical preparation, which is used after dissolving at the time of use.

Currently known compositions and methods for stabilizing thrombin in liquid form are unsatisfactory and include e.g., the following: inclusion of various non-specific components (e.g. bulk carrier proteins such as albumins, different stabilizing sugars, general protease inhibitors etc.); formulations of the thrombin with inhibitors of thrombin activity, which although may be efficient, also inactivate or inhibit the thrombin, thereby reducing its effectiveness; and formulations of a low thrombin concentration solution which necessitate administration of larger amounts of the formulation.

The present invention provides liquid preparations which are advantageous compared with the lyophilized preparations in that they fulfill unmet need of easily administering stable liquid thrombin compositions without an additional step of dissolving in a solvent prior to use. In addition, the present invention provides ready to use pharmaceutical liquid composition comprising liquid thrombin which are advantageous compared to pharmaceutical lyophilized compositions comprising thrombin in that they fulfill unmet need of easily and rapidly administering storage stable liquid thrombin compositions. The term "pharmaceutical liquid" refers to any liquid comprising a substance which has therapeutic or medicinal value.

In a certain aspect, the present invention provides a hemostatic kit comprising:
  a. a container containing a liquid thrombin composition comprising more than 50% v/v glycerol; and
  b. a container containing gelatin.

In some embodiments of the hemostatic kit, the liquid thrombin composition comprises about 60 to about 100% v/v glycerol, or 80 to about 100% v/v glycerol.

In some embodiments of the hemostatic kit, the thrombin solution comprises about 60 to about 100% v/v glycerol, or 80 to about 100% v/v glycerol. In one embodiment of the hemostatic kit, the thrombin solution comprises more than 60%, more than 65%, more than 70%, or more than 75% v/v glycerol, such as 65%, 66%, 67%, 68%, 69%, 70%, 71%, 72%, 73%, 74%, 75%, 76%, 77%, 78%, 79%, 80%, 81%, 82%, 83%, 84%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, including any value and range therebetween.

In some embodiments of the hemostatic kit, the kit further comprises calcium. In some embodiments of the hemostatic kit, the liquid thrombin composition further comprises one or more excipients selected from the group consisting of sodium chloride, mannitol, albumin, and sodium acetate. In some embodiments of the hemostatic kit, the liquid thrombin composition comprises between 1 and about 5,000 IU/ml of thrombin. In some embodiments of the hemostatic kit, the liquid thrombin composition comprises between about 1 to about 2,000, or 100 and about 2,000 IU/ml of thrombin.

In some embodiments of the hemostatic kit, the thrombin in the liquid thrombin composition is at least 70% active after about 20 hours at a temperature of about 50° C. In some embodiments of the hemostatic kit, the thrombin in the liquid thrombin composition is at least 70% active after about 2 minutes at a temperature of about 100° C. The kit may further contain instruction for use.

According to another aspect, the present invention provides a hemostatic composition comprising thrombin, gelatin, and glycerol, and the glycerol is at ratio of above 30% of the solids by weight.

In some embodiments of the hemostatic composition, the composition further comprises calcium. In some embodiments of the hemostatic composition, the composition further comprises one or more excipients selected from the group consisting of sodium chloride, mannitol, albumin, and sodium acetate. In some embodiments of the hemostatic composition, the composition comprises between 1 and about 2,500 IU/ml of thrombin, or about 100 to about 2,000 IU/ml of thrombin. In some embodiments of the hemostatic composition, the composition is for topical use to assist in hemostasis.

According to a further aspect, the present invention provides a method for the large-scale production of a sterile liquid thrombin composition ("the large-scale production method") comprising more than 50% v/v glycerol, the method comprising the following steps:
  a. preparing a thrombin solution by mixing thrombin with a glycerol solution to obtain a solution having more than 50% v/v glycerol;
  b. heating the obtained thrombin solution to at least about 40° C.; and
  c. sterilizing the thrombin solution by passing it through at least one filter having a pore size of about 0.22 μm or less, to thereby obtain a sterile liquid thrombin composition comprising more than 50% v/v glycerol.

In some embodiments of the large-scale production method, the method further comprises a step of viral inactivation performed by heat inactivation. In some embodiments of the large-scale production method, the thrombin solution comprises about 60 to about 100% v/v glycerol or 80 to about 100% v/v glycerol. In one embodiment of the method, the thrombin solution comprises more than 60%, more than 65%, more than 70%, or more than 75% v/v glycerol, such as 65%, 66%, 67%, 68%, 69%, 70%, 71%, 72%, 73%, 74%, 75%, 76%, 77%, 78%, 79%, 80%, 81%, 82%, 83%, 84%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% v/v glycerol, including any value and range therebetween.

In some embodiments of the large-scale production method, the thrombin solution further comprises calcium. In some embodiments of the large-scale production method, the thrombin solution further comprises one or more excipients selected from the group consisting of sodium chloride, mannitol, albumin, and sodium acetate.

In some embodiments of the large-scale production method, the thrombin solution comprises between 1 and about 2,500 IU/ml of thrombin, or about 100 to about 2,000 IU/ml of thrombin. In some embodiments of the large-scale production method, the thrombin in the liquid thrombin composition is at least 70% active after about 20 hours at a temperature of about 50° C. In some embodiments of the large-scale production method, the thrombin in the liquid thrombin composition is at least 70% active after about 2 minutes at a temperature of about 100° C.

According to yet another aspect, the present invention provides a sterile liquid thrombin composition comprising more than 50% v/v glycerol obtained by the method of the invention.

According to an additional aspect, the present invention provides a sterile liquid thrombin composition comprising more than 50% v/v glycerol.

In some embodiments of the sterile liquid thrombin composition, the composition comprises about 60 to about 100% v/v glycerol. In some embodiments the sterile liquid thrombin composition comprises about 60 to about 100% v/v glycerol or 80 to about 100% v/v glycerol. In one embodiment of the sterile liquid thrombin composition, the thrombin solution comprises more than 60%, more than 65%, more than 70%, or more than 75% v/v glycerol, such as 65%, 66%, 67%, 68%, 69%, 70%, 71%, 72%, 73%, 74%, 75%, 76%, 77%, 78%, 79%, 80%, 81%, 82%, 83%, 84%, 75%, 76%, 77%, 78%, 79%, 80%, 81%, 82%, 83%, 84%, 85%, 86%, 87%, 88%, 89%, 90%, 91%, 92%, 93%, 94%, 95, 96%, 97%, 98%, 99%, or 100% v/v glycerol, including any value and range therebetween.

In some embodiments of the sterile liquid thrombin composition, the composition further comprises calcium. In some embodiments of the sterile liquid thrombin composition, the composition comprises one or more excipients selected from the group consisting of sodium chloride, mannitol, albumin, and sodium acetate. In some embodiments of the sterile liquid thrombin composition, the composition comprises between 1 and about 2,500 IU/ml of thrombin, or about 100 to about 2,000 IU/ml of thrombin. In some embodiments of the sterile liquid thrombin composition, the thrombin is at least 70% active after about 20 hours at a temperature of about 50° C. In some embodiments of the sterile liquid thrombin composition, the thrombin is at least 70% active after about 2 minutes at a temperature of about 100° C. In some embodiments of the sterile liquid thrombin composition, the composition further comprises gelatin.

According to yet another aspect, the present invention provides a hemostatic composition comprising thrombin, gelatin, and glycerol at a concentration range above 30% of the solids by weight.

According to yet another aspect, the present invention provides a sealant formulation comprising thrombin and more than 50% v/v glycerol. In some embodiments of the sealant formulation, the formulation comprises about 60 to about 100% v/v glycerol or 80 to about 100% v/v glycerol. In one embodiment of the sealant formulation, the formulation comprises more than 60%, more than 65%, more than 70%, or more than 75% v/v glycerol, such as 65%, 66%, 67%, 68%, 69%, 70%, 71%, 72%, 73%, 74%, 75%, 76%, 77%, 78%, 79%, 80%, 81%, 82%, 83%, 84%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, including any value and range therebetween.

In some embodiments of the sealant formulation, the formulation comprises about 60 to about 100% v/v glycerol or 80 to about 100% v/v glycerol. In some embodiments of the sealant formulation, the formulation further comprises calcium. In some embodiments of the sealant formulation, the formulation comprises between 1 and about 2,500 IU/ml of thrombin, or about 100 to about 2,000 IU/ml of thrombin.

According to yet another aspect, the present invention provides a sterile hemostatic composition comprising thrombin, gelatin, and glycerol at a concentration range above 30% of the solids by weight. In one embodiment of the sterile hemostatic composition, the composition comprises more than 60%, more than 65%, more than 70%, or more than 75% v/v glycerol, such as 65%, 66%, 67%, 68%, 69%, 70%, 71%, 72%, 73%, 74%, 75%, 76%, 77%, 78%, 79%, 80%, 81%, 82%, 83%, 84%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% v/v glycerol, including any value and range therebetween.

According to yet another aspect, the present invention provides a sterile sealant formulation comprising thrombin and more than 50% v/v glycerol.

In some embodiments of the sterile sealant formulation, the formulation comprises 65 to about 100%, 65 to about 100% v/v glycerol, or 80 to about 100% v/v glycerol. In one embodiment of the sterile sealant formulation, the formulation comprises more than 60%, more than 65%, more than 70%, or more than 75% v/v glycerol, such as 65%, 66%, 67%, 68%, 69%, 70%, 71%, 72%, 73%, 74%, 75%, 76%, 77%, 78%, 79%, 80%, 81%, 82%, 83%, 84%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% v/v glycerol, including any value and range therebetween.

In some embodiments of the sealant formulation, the formulation further comprises calcium. In some embodiments of the sealant formulation, the formulation comprises between 1 and about 2,500 IU/ml of thrombin, or about 100 to about 2,000 IU/ml of thrombin.

In some embodiments, the sealant formulation comprises a fibrinogen component.

In some embodiments in any aspect of the kit, compositions, formulations, and methods provided herein, the kit, compositions, and/or formulations are at least two-component kit, two-component compositions, and two-component formulations, respectively. In some embodiments of any aspect of the two-component compositions, and two-component formulations, one of the components comprises fibrinogen.

For example, the kit may be applied using an applicator device and may be used for administering several and sequential injections of the at least two-component substance (e.g. a fibrin sealant such as EVICEL). In one embodiment, the applicator device enables multiple injections of a fixed-dose of the mixed components on a 2-D surface of a tissue while moving the device. In one embodiment, the applicator has an injection needle, which is optionally automatically retracted from the patient's skin after the injection is completed without the need for the administrator to lift the device upward from the injection surface. In one embodiment, the kit may be used for the administration of fibrin sealant with a fibrinogen component and a thrombin component in any embodiments of any aspect thereof.

As used herein and in the art, the term "fibrinogen" refers to a precursor protein of the blood clot matrix. The fibrinogen has a molecular weight of about 340,000 Daltons and consists of 3 pairs of non-identical polypeptide chains, Aα, Bβ and γ, linked together by disulfide bonds. Typically, fibrinogen has a trinodular structure: two identical D terminal globular domains and a central E globular domain connected by supercoiled α-helices.

In some embodiments, the fibrinogen is or originates from fibrinogen concentrate. In some embodiments, the fibrinogen is a blood derived fibrinogen concentrate.

Hereinthroughout, the terms "originates from", or "derived from", are used interchangeably and refer to an origin or source of the relevant component, which may include naturally occurring, recombinant, processed, unpurified or purified molecules (e.g., the relevant protein). In some embodiments, the fibrinogen comprises cryoprecipitated fibrinogen. In some embodiments, the fibrinogen originates from cryoprecipitated fibrinogen. In some embodiments, the fibrinogen solution component and the thrombin solution are combined in a ratio (v/v) of 1:2 to 2:1, e.g., about 1:1.

In some embodiments, the cryoprecipitated fibrinogen is regarded as the biologically active component (BAC) of blood plasma. In some embodiments, the BAC is viral inactivated. In some embodiments, BAC is a biologically active component that comprises an antifibrinolytic agent such as, without being limited thereto, tranexamic acid. A non-limiting exemplary BAC comprising tranexamic acid is a product named "Quixil" (Omrix, Israel). This is considered as a second-generation BAC and is referred to in the art as "BAC2". During BAC2 preparation, plasminogen (the enzyme precursor of plasmin, which breaks down fibrinogen and fibrin) is removed. Non-limiting preparation routes of BAC are described in U.S. Pat. No. 6,121,232 and/or WO 1998033533, the contents of which is incorporated by reference. In some embodiments, a BAC composition comprises one or more anti-fibrinolytic agents (e.g., tranexamic acid) and arginine hydrochloride. In some embodiments, the concentration of the anti-fibrinolytic agent, such as tranexamic acid in the BAC, ranges from about 80 to about 110 mg/ml. In some embodiments, BAC2 is prepared according to the disclosure of EP 534178, the content of which is incorporated herein by reference. For example, BAC2 may be prepared from concentrated cryoprecipitate, which thereafter undergoes viral inaction e.g., by solvent detergent treatment and pasteurization. In view of removal of plasmin/plasminogen from the cryoprecipitate, there is no need to add anti-fibrinolytic agents, such as tranexamic acid, aprotinin or the like. Accordingly, in some embodiments, the BAC2 does not comprise tranexamic acid.

Several hemostatic materials, such as, SURGICEL®, may be effectively used in combination with the disclosed kit and/or thrombin formulations. For example, the disclosed thrombin solution may be added to a gelatin, e.g., flowable gelatin matrix prior to use. Once the gelatin is mixed with the thrombin formulation, an appropriate applicator tip may be attached to a syringe for product delivery onto the bleeding site or tissue, or as an aid to hemostasis whenever oozing blood and minor bleeding from capillaries and small venules is accessible and control of bleeding.

The term "tissue" refers to an association of cells and/or cell components united in carrying out a particular function. The cells in the tissue may be all of one type or of more than one type. The tissue can be an artificial tissue in which cells are grown to function in a similar manner as a tissue in a living organism. The tissue may be a human body tissue or an animal tissue.

The two-component composition may be provided by combining (e.g., upon mixing) the two components, thereby obtaining a composition, and simultaneously, or thereafter, applying the obtained composition directly to the site where bleeding reduction or prevention is needed. In some embodiments, the application of the composition is assisted by spraying or dripping the composition onto the area to be treated.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

FIG. 2A presents the activity measured at 3 and 6 months at 25° C. FIG. 2B presents the activity measured at 12 months at 4° C. Top bars herein and in bar graphs presented below represent standard deviation.

DESCRIPTION OF EMBODIMENTS OF THE INVENTION

Thrombin is widely used as a hemostatic material to control bleeding; however, it is an autocatalytic enzyme and is therefore unstable in its liquid form. The duration of liquid thrombin stability is diminished as the thrombin concentration increased and/or as the temperature rises. As a result, commercial preparations of thrombin exist as a powder or a frozen liquid. This has some disadvantages, including a relatively long preparation time since powder thrombin must be reconstituted and frozen thrombin must be thawed; shipping restrictions due to the need to ship at a low temperature; as well as potentially compromised sterility if preparation requires reconstitution of the powder thrombin.

As used herein, the term "powder" refers to a plurality of particles of a solid characterized by small size, typically, within the range of from 0.1 to 1000 micrometers.

The term "solid" characterizes the state of the compound or composition at room temperature (e.g., 25° C.) and at atmospheric pressure (760 mmHg), i.e. a compound or a composition of high consistency which retains its form during storage. This term in the present application also relates to non-fluid particles, or dissolved substance. As opposed to "liquid" compounds and compositions, the solid does not flow under its own weight.

As used herein, "thrombin" denotes an activated enzyme which results from the proteolytic cleavage of prothrombin (factor II). Thrombin may be produced by a variety of methods of production known in the art, and includes, but is not limited to, recombinant thrombin and plasma derived thrombin. Human thrombin is a 295 amino acid protein composed of two polypeptide chains joined by a disulfide bond. Both human and non-human (e.g., bovine) thrombin may be used within the scope of the present disclosure.

The origin for thrombin used in this invention may be from one or several sources including but not limited to: recombinant bacteria and/or cells (Vu et al., 2016, J. Viet. Env. 8(1):21-25), whole blood (pooled from several donations or not) and/or blood fraction (that may be pooled from several donations, e.g. plasma). Thrombin is available by manufacturers such as Johnson and Johnson, Baxter and CSL Behring either as a standalone product, e.g. EVI-THROM®, or as a component of a product e.g. EVICEL®, TISEEL®, Beriplast®, and the like.

The inventors have surprisingly found that high concentrations of glycerol, above 50% v/v in the thrombin solution, result in increased stability of the thrombin enzyme e.g., at elevated temperatures, as well as enhanced thrombin activity in vivo.

Figure 1:
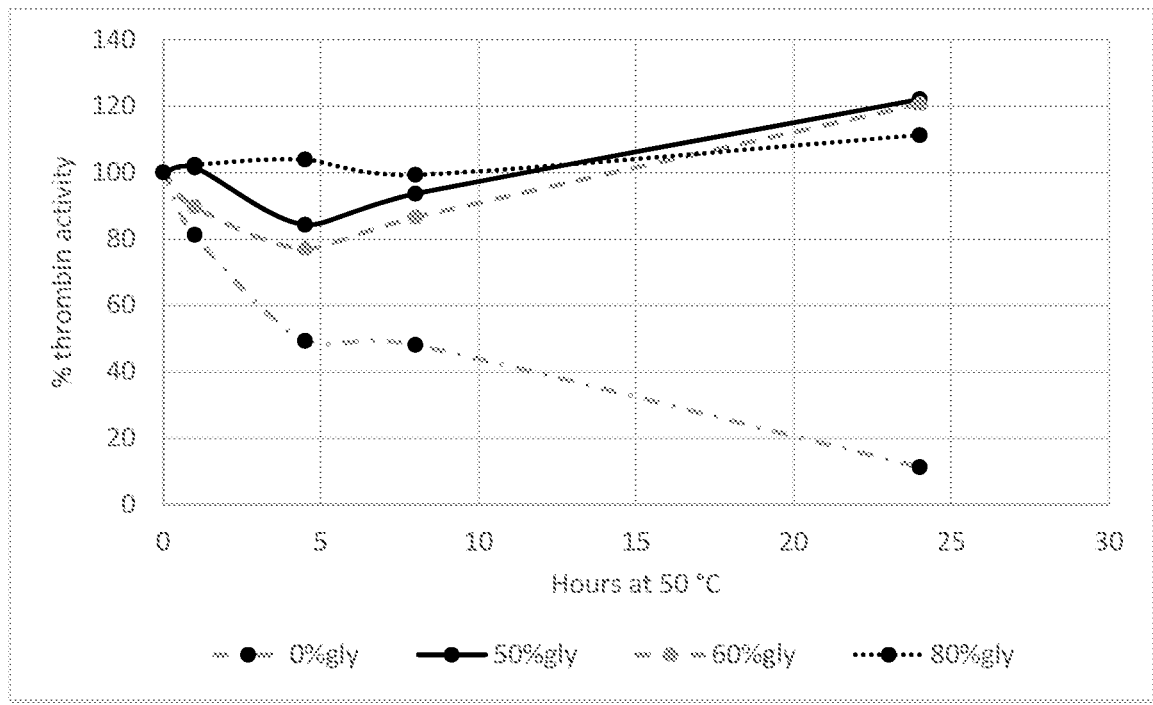
FIG. 1 shows graphs presenting the effect of various glycerol concentrations on thrombin activity at 50° C. for 24 hours (h). Thrombin was suspended in several different concentrations of glycerol in double distilled water (DDW) and placed at 50° C. for 24 hours. Activity was measured at 1, 4.5, 8 and 24 h. solid gray line with dots: 0% glycerol; solid black line: 50% v/v glycerol; dashed gray line: 60% v/v glycerol; dotted line: 80% v/v glycerol; n=4.
Figure 3:
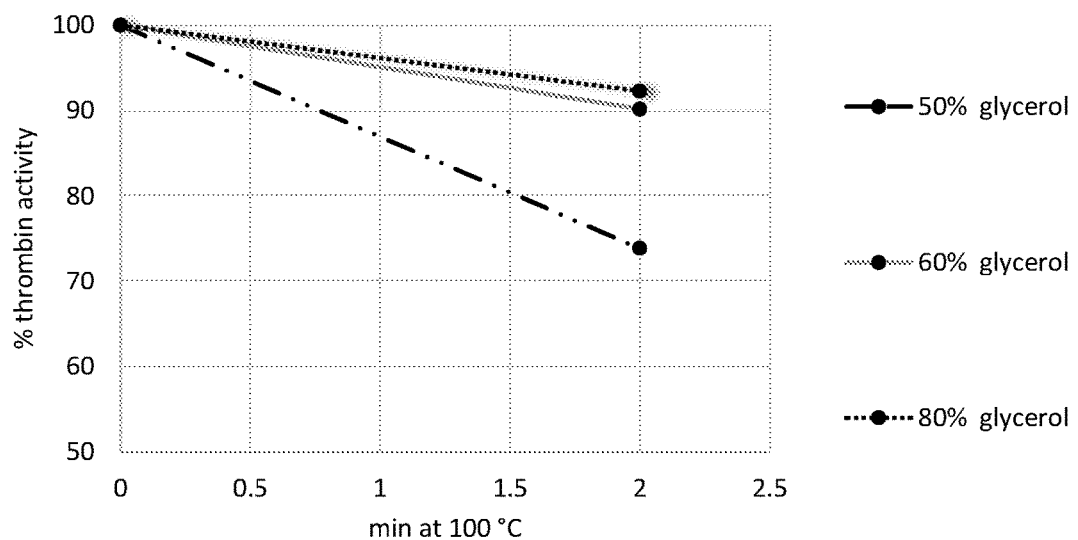
FIG. 3 shows graphs presenting the effect of various glycerol concentrations on thrombin activity at 100° C. (measured after 2 min). Thrombin was suspended in several different concentrations of glycerol in DDW, and placed at 100° C. Activity was measured after 2 minutes. solid black line with dots: 50% v/v glycerol; solid gray line: 60% v/v glycerol; dotted line: 80% v/v glycerol; n=2.

As shown in FIG. 1, while thrombin prepared without glycerol loses about 90% activity after 24 hours at 50° C., the activity of thrombin with 50% glycerol or more is fully maintained. Additionally, FIG. 3 shows that after 2 minutes at 100° C., which normally completely reduces the enzyme activity, 75% activity is maintained with 50% glycerol, and at least 90% activity is maintained with 60% or with 80% glycerol. This increased stability at elevated temperatures allows to use liquid thrombin in ways that were not possible before, such as shipping, handling, and storing in liquid state without the need for refrigeration. Further, Example 3 below demonstrates that glycerol, which is generally considered too viscous for filter sterilization, can be effectively filtered at temperatures of 40° C. and 50° C. Combining the above results allows the sterilization by filtration of liquid thrombin in a solution containing a high glycerol concentration (e.g., above 60% by weight) by elevating the temperature of filtration as described herein.

The term "filter", and any grammatical inflection thereof, means intercept, hinder, impede or interfere with the passage of particles in a fluid, e.g., liquid stream.

However, a potential problem is that a viscous medium such as glycerol may interfere with the interaction of thrombin with its target molecules and therefore affect formation, kinetics or quality of the clot formed. Based on this, a person skilled in the art would not have conceived of combining thrombin with a high glycerol concentration.

Nevertheless, as was surprisingly found by the inventors, the situation is different in vivo. FIG. 3 describes in vivo activity of gelatin prepared with a liquid thrombin solution comprising glycerol. A gelatin kit (Surgiflo®) comprises gelatin and thrombin powder being mixed together just prior to application in/on a bleeding site. Since thrombin is provided in a powdery state, it requires reconstitution by the practitioner.

Figure 4:
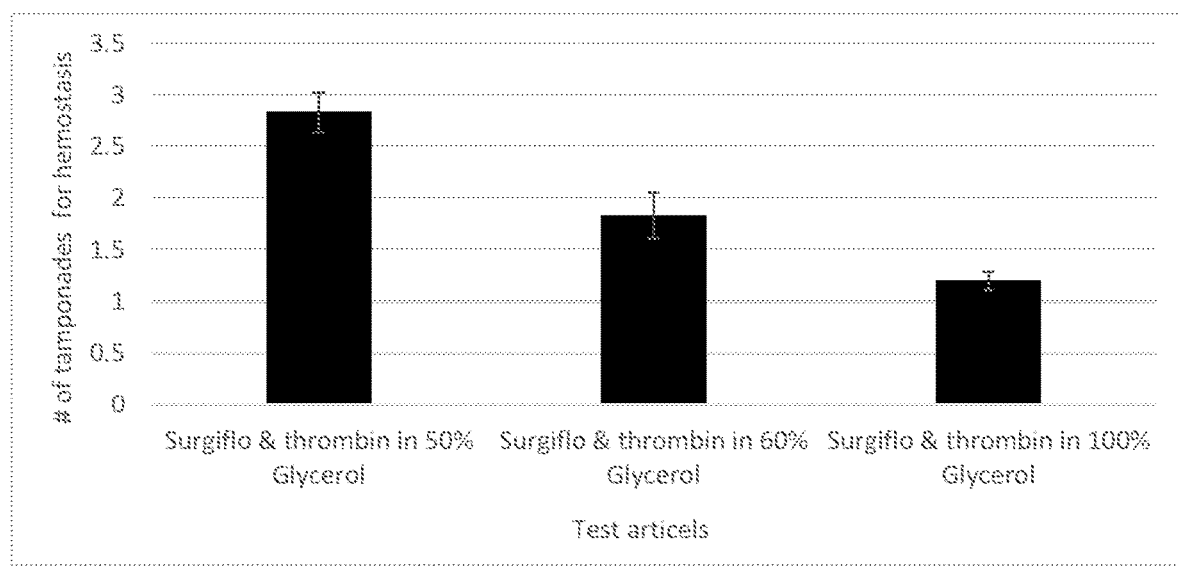
FIG. 4 shows a bar graph presenting the effect of various glycerol concentrations on thrombin activity in vivo in a porcine punch biopsy model. Thrombin was suspended in the indicated concentrations of glycerol in DDW; and used instead of the reconstituted thrombin in a gelatin kit to prepare a gelatin paste comprising thrombin at various glycerol concentrations. Thrombin activity was measured according to the number of tamponades needed to stop bleedings; from left: gelatin paste with thrombin in 0 v/v glycerol; gelatin paste with thrombin in 50% v/v glycerol; gelatin paste with thrombin in 60% v/v glycerol; and gelatin paste with thrombin in 100% v/v glycerol; n=5.

In contrast to the issues of viscosity discussed above, it was found that increased glycerol concentrations in thrombin reconstituted with glycerol, corresponded to enhanced ability of the formulation to reduce bleeding, as shown in FIG. 4. Additionally, an important advantage of the liquid thrombin formulation of the invention is saving the step of reconstitution, thereby preventing the hassle and saving time for the practitioner as well as minimizing a risk of contamination.

The terms "liquid thrombin composition", "liquid thrombin solution", "thrombin solution" and "liquid thrombin formulation" are used hereinthroughout interchangeably, and refer to a liquid composition comprising thrombin. In some embodiments the "liquid thrombin composition" is an aqueous solution, i.e. comprises 1 to less than 50% water (% v/v).

The term "liquid" refers to a substance that can flow, has no fixed shape, and is not a solid or a gas.

Consequently, the stable liquid thrombin composition of the invention may be used to replace the powdered or the frozen thrombin as a hemostatic material. The liquid thrombin of the invention may be provided as a stand-alone thrombin solution, e.g., a sterile and stable stand-alone thrombin solution, or as part of a kit, such as in the Surfiglo® kit, or a fibrin sealant kit instead of the thrombin components in these kits.

Accordingly, the present invention provides in one aspect a hemostatic kit comprising a container containing a liquid thrombin composition comprising more than 50% v/v glycerol; and a container containing gelatin. The present invention also provides a hemostatic kit comprising a container containing a storage stable sterile liquid thrombin composition comprising more than 50% v/v glycerol; and a container containing gelatin.

The term "storage stable" is to be understood as referring to the formulation, composition, optionally being present in a container e.g., vial, that is stable under preselected storage conditions (see below), including pre-selected storage temperature, pre-selected physical state of the formulation (e.g., fluid/liquid). Stability can be determined by methods known in the art, e.g., by testing the absence of visible aggregations and/or fibrin clots in the formulation under the pre-selected storage condition, for example, when the formulation is in liquid form. Further, in accordance with the present disclosure, when referring to a stable sealant formulation it is to be understood as one that, upon use, has an effective clotting time irrespective of the formulation's storage conditions, e.g., the sealant formulation clots at essentially the same time period irrespective of whether it was stored at room temperature (e.g., 8 to 40° C.) or at lower temperatures (e.g., below 8° C.).

In some embodiments, the pre-selected storage conditions comprise storage at room temperature (e.g., 10 to 30° C.) and the sealant formulation is stable for at least 5 minutes, at times for at least 15 minutes, or for at least 1 hour, for at least a day, at least 2, 3, 4, 5, 6 or even 7 days, at times for e.g., 1, 2, 3, 4, 5, 6, 7, 8, 9, 10, 11, 12, 13, 14, 15, 16, 17, 18, 19, 20, 21, 22, 23, or even 24 months, or more, including any value and range therebetween.

In some embodiments, the pre-selected storage conditions comprise storage at low temperature (e.g., 2 to 10° C.) and the sealant formulation is stable for at least 5 minutes, at times for at least 15 minutes, or for at least 1 hour, for at least a day, at least 2, 3, 4, 5, 6 or even 7 days, at times for e.g., 1, 2, 3, 4, 5, 6, 7, 8, 9, 10, 11, 12, 13, 14, 15, 16, 17, 18, 19, 20, 21, 22, 23, or even 24 months, or more, including any value and range therebetween.

The term "container" may refer to any generic structure such as a vessel or a vial, that may contain e.g., a liquid.

In one embodiment, this kit is stored at room temperature, such as in a temperature in the range of 8 to 40° C.

In another aspect, the present invention provides a hemostatic kit for storage at 2 to 8° C., comprising a container containing a liquid thrombin composition comprising more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, or more than 90% v/v glycerol, e.g., 60% to 100%, or 80% to 100% v/v glycerol; and a container containing gelatin.

The hemostatic kit of the invention may be a kit for use in reducing, preventing or stopping blood flow, e.g., in open wounds, and it may be used for reducing, preventing or stopping blood flow during a procedure, such as during a surgical procedure such as, for example, laparoscopic surgery, neurosurgery, abdominal surgery, cardiovascular surgery, thoracic surgery, head and neck surgery, pelvic surgery and skin and subcutaneous tissue procedures. The kit may be used for reducing or preventing blood flow from the skin, or in internal organs.

The term "liquid solution" also encompasses a viscous solution. The term "viscous solution" refers to a solution that has an increased resistance to flow, yet is capable of flowing, typically, but not exclusively, having a viscosity greater than about 1 centipoise unit and is less than about 10,000 centipoise units.

The liquid thrombin composition for the kit may be sterile and obtained from large-scale production method comprising the following steps:
 a. preparing a thrombin solution by mixing thrombin with a glycerol solution to obtain a solution having more than 50% v/v glycerol;
 b. heating the obtained thrombin solution to at least 40° C.; and
 c. sterilizing said thrombin solution by passing it through at least one filter having a pore size of 0.22 μm or less,
to thereby obtain a liquid sterile thrombin solution comprising more than 50% v/v glycerol.

The term "large-scale" as used herein relates to a process in which at least 1 liter of solution is produced, typically comprising at least about 400 IU of thrombin.

The gelatin source for the invention may be synthetic (e.g., recombinant gelatin) or derived from animals such as pigs. The gelatin source may be sterile and may come in different forms, such as, paste, powder or sponge. The term "paste" as used herein, relates to the consistency of the composition at at-least one temperature around the room temperature, and may refer to a fluid mixture of solid particles.

The gelatin used in the invention may be cross-linked prior to its use. Cross-linking of the gelatin may be performed by any number of suitable methods disclosed in the art. For example, gelatin can be crosslinked by heating to 150° C. for 3 hours (Nagura et al., 2002, Polymer Journal 34: 761-766).

In some embodiments, the gelatin is dissolved in a solvent to form a gelatin paste. In some embodiments, the gelatin paste comprises glycerol. In some embodiments, the gelatin paste comprises glycerol at more than 30% of the solids by weight.

In some embodiments, the liquid thrombin composition is sterile.

In some embodiments, the liquid thrombin composition comprises more than 50% v/v glycerol. In some embodiments, the liquid thrombin composition comprises at least about 55%, at least about 60%, at least about 65%, at least about 70%, at least about 75%, at least about 80%, at least about 85%, at least about 90%, or at least about 95% v/v glycerol, including any value and range therebetween. In some embodiments, the liquid thrombin composition comprises 100% v/v glycerol. In some embodiments, the liquid thrombin composition comprises between about 50% and about 80% v/v glycerol. In some embodiments, the liquid thrombin composition comprises between about 60% and about 80% v/v glycerol. In some embodiments, the liquid thrombin composition comprises between about 60% and about 100% v/v glycerol. In some embodiments, the liquid thrombin composition comprises between about 70% and about 100% v/v glycerol. In some embodiments, the liquid thrombin composition comprises between about 80% and about 100% v/v glycerol. In some embodiments, the liquid thrombin composition comprises more than 65%, more than 67%, or more than 70%, and up to about 100% (by solvent volume) % v/v glycerol.

Unless stated otherwise, the definition of glycerol concentration as "% v/v", or "%" in the context of glycerol, relates to the percentage of the glycerol volume out of the total volume of the solvents (e.g., water) in liquid thrombin composition. As used herein, the term "solvent" refers to a material that dissolves or disperse another substance while not changing its physical state.

Calcium is an important element in the clotting cascade. Calcium is needed for activation of factor XIII into factor XIIIa, which cross-links and stabilizes fibrin to generate an insoluble clot.

Accordingly, in some embodiments, the disclosed kit and/or compositions in embodiments thereof further comprise calcium. Calcium used with the invention may be in the form of a salt, e.g., calcium chloride salt. Alternatively, additional salts may be used, such as calcium acetate and/or calcium citrate. In the kit, the calcium salt may be provided in the liquid thrombin composition. Alternatively, the calcium salt may be provided in the kit in a separate container, or the calcium salt may be provided in the kit in the same container containing the gelatin component.

The liquid thrombin composition in any aspect disclosed herein may comprise one or more of the following excipients: calcium, albumin, saccharides, saccharides derivatives, polyol(s), acetate, citrate, amino acids, polyethylene glycol, sodium chloride, and water. The calcium source may be calcium chloride and may be in a concentration range of 2-60 mM. The albumin may be in a concentration range of 0.05-1% (w/v) or in a range of 0.5-1% (w/w). The saccharides source may be saccharose and may be in a 5 g/l concentration. The saccharides derivatives source may be gluconic acid. The polyol(s) source may be mannitol and may be in a 2% (w/w) concentration. The acetate source may be sodium acetate and may be in a 10 mM concentration. The citrate source may be sodium citrate. The amino acids may be histidine and may be in a 10 mM concentration. The polyethylene glycol source may be PEG-3350 and may be e.g., in a 0.03% concentration. The sodium chloride may be in a range of 50-175 mM.

The thrombin solution may be at a pH range of about 5.0-8.5.

The term "excipient" as used herein denotes a non-therapeutic agent added to a pharmaceutical composition e.g., to provide a desired consistency or stabilizing effect.

Examples of thrombin solutions comprise, without limitation: 800-1200 IU of thrombin/ml, 20 mM sodium acetate, 40 mM $CaCl_2$), 110 mM NaCl, 0.5% w/w human albumin, and 2% w/w mannitol at a pH of 6.8 to 7.2; calcium chloride (40 μmol/ml), albumin (human), sodium chloride, water for injection; 500 IU/ml of protein thrombin, 1% albumin, 10 mM sodium acetate, and 75 mM sodium chloride; 500 IU/ml of thrombin, 2% mannitol, 10 mM histidine, 0.03% of PEG-3350, and 175 mM of sodium chloride; 500 IU of thrombin/ml human albumin at a concentration of between 0.1% and 1% (w/v) and sodium chloride at a concentration of 0.05 M at a pH of between 5.0 and 8.5.

The albumin is e.g., human albumin. However, the albumin may also be from a non-human source, or recombinant albumin. In some embodiments of any aspect disclosed herein, the liquid thrombin composition comprises water for injection.

Accordingly, in some embodiments, the liquid thrombin composition further comprises excipients selected from, without being limited thereto, sodium chloride, mannitol, albumin, and sodium acetate.

Concentrated purified thrombin in liquid form displays a reduction in activity during prolonged storage, mostly as a result of autocatalytic cleavage. For example, aqueous liquid thrombin at a concentration of 1000 international units (IU)/ml may undergo autocatalytic cleavage at room temperature causing a significant loss of thrombin activity.

In some embodiments, the thrombin solution or composition comprises 1-10,000, or 100-10,000 IU thrombin/ml such as 100-4000, or 100-2500 IU thrombin/ml. As used hereinthroughout, the term "IU" denotes "International Units" and may be determined by the clotting assay against an internal reference standard for potency concentration measurement that has been calibrated against, for example, the World Health Organization (WHO) Second International Standard for Thrombin, 01/580. A unit (U) is equivalent to an International Unit (IU).

In commercial preparations, thrombin is typically used at about 400-1,200 IU/ml.

Accordingly, in some embodiments, the liquid thrombin composition of the invention comprises between 1 and 2,500 IU/ml of thrombin. In some embodiments, the thrombin composition comprises between 100 and 2,000 IU/ml of thrombin In some embodiments, the thrombin composition comprises between 400 and 1,200 IU/ml of thrombin. In some embodiments, the thrombin composition comprises between 800 and 1,200 IU/ml of thrombin. In some embodiments, the thrombin composition comprises between 400 and 800 IU/ml of thrombin. In some embodiments, the thrombin composition comprises between 400 and 600 IU/ml of thrombin.

In some embodiments, the concentration of thrombin is between about 1 and about 20 μM. In some embodiments, the concentration of thrombin is between about 5 and about 15 μM. In some embodiments, the concentration of thrombin is between about 5 and about 10 μM.

As discussed above, thrombin is an autocatalytic enzyme and therefore unstable in liquid form. The stability decreases as the thrombin concentration or the temperature increase. Surprisingly, the liquid thrombin compositions of the invention, which include more than 50% glycerol, are stable at very high temperatures as described herein, which facilitates sterilization, viral inactivation by heat, shipping, storage, and handling of the liquid thrombin without refrigeration.

The terms "stability" or "stable" as used herein relate to the activity of the thrombin enzyme following exposure to a certain temperature. Generally, a liquid thrombin composition is defined as stable after certain duration at a certain temperature if the thrombin is at least 70% active.

Accordingly, in some embodiments the thrombin in the liquid thrombin composition is at least 70% active after 24 hours at a temperature of about 50° C. In some embodiments, the thrombin in the liquid thrombin composition is at least 75%, at least 80%, at least 85%, at least 90%, at least 95%, or 100% active after 24 hours at a temperature of about 50° C.

In some embodiments, the liquid thrombin composition comprises more than 50% glycerol and the thrombin in the liquid thrombin composition is at least 70% active after 24 hours at a temperature of about 50° C. In some embodiments, the thrombin composition comprises more than 60% glycerol and the thrombin in the liquid thrombin composition is at least 70% active after 24 hours at a temperature of about 50° C. In some embodiments, the thrombin composition comprises more than 80% glycerol and the thrombin in the liquid thrombin composition is at least 70% active after 24 hours at a temperature of about 50° C.

In some embodiments, the liquid thrombin composition comprises more than 50% glycerol and the thrombin in the liquid thrombin composition is at least 80% active after 24 hours at a temperature of about 50° C. In some embodiments, the thrombin composition comprises at least 60% glycerol and the thrombin in the liquid thrombin composition is at least 80% active after 24 hours at a temperature of about 50° C. In some embodiments, the thrombin composition comprises at least 80% glycerol and the thrombin in the liquid thrombin composition is at least 80% active after 24 hours at a temperature of about 50° C.

In some embodiments, the liquid thrombin composition comprises more than 50% glycerol and the thrombin in the liquid thrombin composition is at least 90% active after 24 hours at a temperature of about 50° C. In some embodiments, the thrombin composition comprises at least 60% glycerol and the thrombin in the liquid thrombin composition is at least 90% active after 24 hours at a temperature of about 50° C. In some embodiments, the thrombin composition comprises at least 80% glycerol and the thrombin in the liquid thrombin composition is at least 90% active after 24 hours at a temperature of about 50° C.

Figure 2A:
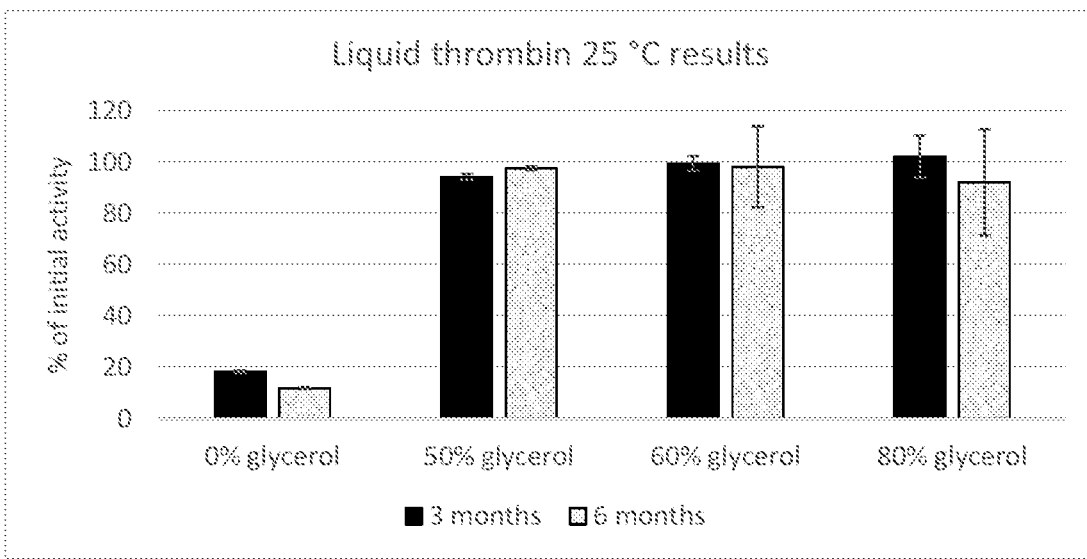
FIGS. 2A-B show bar graphs presenting the effect of various glycerol concentrations on thrombin activity at 25° C. and 4° C. Thrombin was suspended in several different concentrations of glycerol in DDW and placed at 25° C. for 6 months and at 4° C. for 12 months.
Figure 2B:
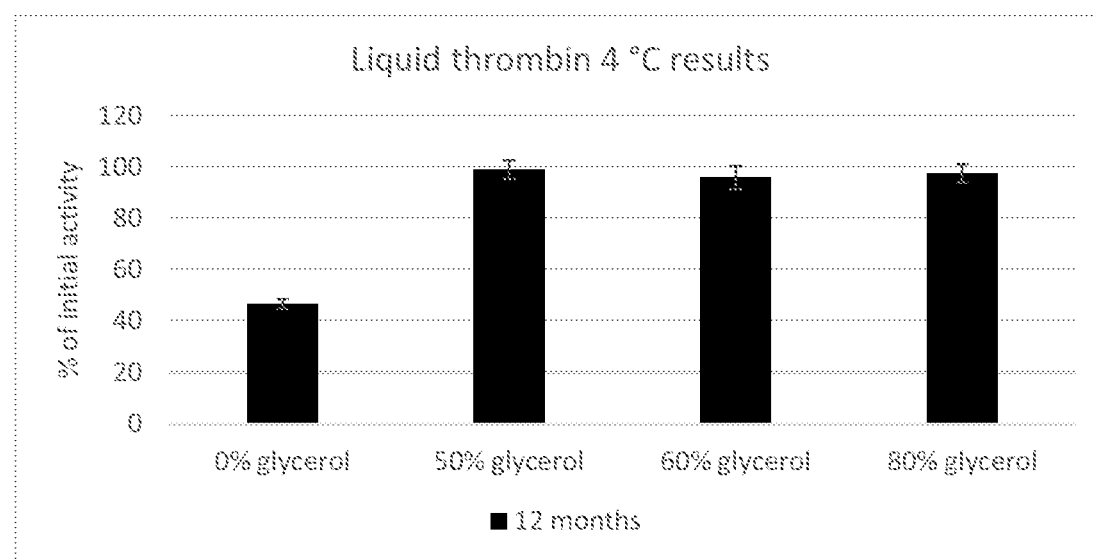

Reference is now made to FIGS. 2A-B presenting the effect of various glycerol concentrations on thrombin activity at various temperatures. Accordingly, in some embodiments, the thrombin in the liquid thrombin composition is at least 70% active after at least 6 months at a temperature of about 25° C. In some embodiments, the thrombin in the liquid thrombin composition is at least 50%, at least 75%, at least 80%, at least 85%, at least 90%, at least 95%, or 100% active after at least 6 months at a temperature of about 25° C.

By "at least 6 months" it is meant to refer e.g., to 6 months, 7 months, 8 months, 9 months, 10 months, 11 months, 12 months, 13 months, 14 months, 15 months, or more, including any value and range therebetween.

By "at least 50%" it is meant to refer e.g., to 50%, 55%, 60%, 65%, 60%, 65%, 70%, 75%, 80%, 85%, 90%, 95%, or 100%, including any value and range therebetween.

In some embodiments, the liquid thrombin composition comprises more than 50% glycerol and the thrombin in the liquid thrombin composition is at least 70% active at least 6 months at a temperature of about 25° C. In some embodiments, the thrombin composition comprises more than 60% glycerol and the thrombin in the liquid thrombin composition is at least 70% active after at least 6 months at a temperature of about 25° C. In some embodiments, the thrombin composition comprises more than 80% glycerol and the thrombin in the liquid thrombin composition is at least 70% active after at least 6 months at a temperature of about 25° C.

In some embodiments, the liquid thrombin composition comprises more than 50% glycerol and the thrombin in the liquid thrombin composition is at least 80% active after at least 6 months at a temperature of about 25° C. In some embodiments, the thrombin composition comprises at least 60% glycerol and the thrombin in the liquid thrombin composition is at least 80% active after at least 6 months at a temperature of about 25° C. In some embodiments, the thrombin composition comprises at least 80% glycerol and the thrombin in the liquid thrombin composition is at least 80% active after at least 6 months at a temperature of about 25° C.

In some embodiments, the thrombin in the liquid thrombin composition is at least 70% active after at least 6 months at a temperature of about 0° C. In some embodiments, the thrombin in the liquid thrombin composition is at least 75%, at least 80%, at least 85%, at least 90%, at least 95%, or 100% active after at least 6 months at a temperature of about 0° C.

In some embodiments, the liquid thrombin composition comprises more than 50% glycerol and the thrombin in the liquid thrombin composition is at least 70% active at least 6 months at a temperature of about 0° C. In some embodiments, the thrombin composition comprises more than 60% glycerol and the thrombin in the liquid thrombin composition is at least 70% active after at least 6 months at a temperature of about 0° C. In some embodiments, the thrombin composition comprises more than 80% glycerol and the thrombin in the liquid thrombin composition is at least 70% active after at least 6 months at a temperature of about 0° C.

In some embodiments, the liquid thrombin composition comprises more than 50% glycerol and the thrombin in the liquid thrombin composition is at least 80% active after at least 6 months at a temperature of about 0° C. In some embodiments, the thrombin composition comprises at least 60% glycerol and the thrombin in the liquid thrombin composition is at least 80% active after at least 6 months at a temperature of about 0° C. In some embodiments, the thrombin composition comprises at least 80% glycerol and the thrombin in the liquid thrombin composition is at least 80% active after at least 6 months at a temperature of about 0° C.

In some embodiments, the thrombin in the liquid thrombin composition is at least 70% active after 2 minutes at a temperature of about 100° C. In some embodiments, the thrombin in the liquid thrombin composition is at least 75%, at least 80%, at least 85%, at least 90%, at least 95%, or 100% active after 2 minutes at a temperature of about 100° C. In some embodiments, the liquid thrombin composition comprises more than 50% glycerol and the thrombin in the liquid thrombin composition is at least 70% active after 2 minutes at a temperature of about 100° C. In some embodiments, the thrombin composition comprises at least 60% glycerol and the thrombin in the liquid thrombin composition is at least 70% active after 2 minutes at a temperature of about 100° C. In some embodiments, the thrombin composition comprises at least 80% glycerol and the thrombin in the liquid thrombin composition is at least 70% active after 2 minutes at a temperature of about 100° C.

In some embodiments, the liquid thrombin composition comprises at least 60% glycerol and the thrombin in the liquid thrombin composition is at least 80% active after 2 minutes at a temperature of about 100° C. In some embodiments, the thrombin composition comprises at least 80% glycerol and the thrombin in the liquid thrombin composition is at least 80% active after 2 minutes at a temperature of about 100° C.

In some embodiments, the liquid thrombin composition comprises at least 60% glycerol and the thrombin in the liquid thrombin composition is at least 90% active after 2 minutes at a temperature of about 100° C. In some embodiments, the thrombin composition comprises at least 80% glycerol and the thrombin in the liquid thrombin composition is at least 90% active after 2 minutes at a temperature of about 100° C.

In some embodiments, the thrombin in the disclosed liquid thrombin compositions is at least 70% active after 24 months at room temperature (e.g., about 25° C.). In some embodiments, the thrombin in the disclosed liquid thrombin compositions is at least 75%, at least 80%, at least 85%, at least 90%, at least 95%, or 100% active after 24 months at room temperature. In some embodiments the thrombin in the liquid thrombin composition of the invention is at least 75%, at least 80%, at least 85%, at least 90%, at least 95%, or 100% active after 24 months at a temperature of 2-8° C. In some embodiments, the thrombin in the disclosed liquid thrombin composition is at least 70% active after 24 months at a temperature of 2 to 8° C.

In some embodiments, the thrombin in the liquid thrombin composition of the invention is at least 70% active after 2 years at −20° C.

In some embodiments, the thrombin in the liquid thrombin composition of the invention is at least 70% active after 3 years at −20° C.

In some embodiments, the hemostatic kit comprises a syringe containing the liquid thrombin composition and a syringe containing the gelatin. In some embodiments, at least one of the containers in the kit is a pre-filled syringe. In some embodiments, a syringe is provided in addition to the containers of the kit. In some embodiments, the container is in a specific type, such as a vial or an applicator.

The kit described above may comprise a thrombin component and a gelatin component, which are mixed together before application. For example, the components are mixed by a surgeon or another practitioner when there is a need to reduce bleeding, e.g., during an operation. The mixing of the components of the kit forms a hemostatic composition.

Accordingly, in an additional aspect, the present invention provides a hemostatic composition comprising thrombin, gelatin, and glycerol in a range of above 30% of the solids in the hemostatic composition by weight.

In some embodiments, the hemostatic composition comprises glycerol at more than more than 31%, more than 35%, more than 40%, more than 45%, more than 50%, more than 55%, more than 60%, more than 65%, more than 70%, more than 75%, more than 80%, more than 85%, more than 90%, more than 95%, or approaching 100% of the solids by weight.

In some embodiments, the prominent solid in the hemostatic compositions described herein is gelatin.

In a further aspect, the present invention provides the hemostatic composition of the invention for topical use to assist in hemostasis.

Hemostasis (or haemostasis) is the first stage of wound healing. It is a process which causes bleeding to stop. By "assist in hemostasis" it is meant to help reduce or stop bleeding.

In an additional aspect, the present invention provides a pharmaceutical composition comprising thrombin and gelatin, glycerol at above 30% of the solids by weight, and a pharmaceutically acceptable excipient.

Excipients, e.g., for pharmaceutical composition, are described herein above, and may further include any pharmaceutically suitable excipient, such as calcium chloride, human albumin, mannitol, sodium acetate, sodium chloride, sodium citrate dihydrate, gluconate buffer, saccharose, glycine, sodium acetate, histidine, and PEG.

Any preparation for therapeutic use must be sterile. Especially when handling blood products, the sterility issue is crucial, and specifically the issue of viral inactivation. In general, viral inactivation may be carried out by any method, including, e.g., solvent detergent, heat inactivation, irradiation, and nanofiltration, or any combination thereof. Typically, the standard for viral inactivation requires using two different methods. Additionally, the Food and Drug Administration (FDA) standard for sterility requires filtration.

However, since liquid thrombin is unstable, especially at high temperatures, sterilization of liquid thrombin is impractical using heat inactivation or irradiation, due to their negative effect on thrombin activity. On the other hand, preparations of thrombin that comprises high concentrations of glycerol and are therefore more stable, are too viscous for sterilization by filtration at room temperature. The surprising finding of the present invention that thrombin preparations including glycerol are not only stable at high temperatures, but also have an enhanced activity in vivo compared to preparations not including glycerol, facilitates sterilization by filtration at high temperatures, in which the glycerol is less viscous. This allows for the large-scale production of a sterile and stable liquid thrombin composition comprising glycerol. Additionally, the stability of glycerol-containing liquid thrombin at elevated temperatures allows also viral inactivation by heat treatment.

The term "sterile" as used herein means having a low bioburden, effectively being germ-free, e.g., being free from microorganisms, e.g., bacteria and viruses. Sterilization is the process of reducing the bioburden to an effectively germ-free level. A sterile liquid is generally defined as a liquid that underwent sterile filtration. Accordingly, in some embodiment, a sterile thrombin solution or a sterile liquid thrombin composition is a thrombin solution or a liquid thrombin composition which has been sterilized by sterile filtration, e.g., by passing through a filter of 0.22 µm or less.

As discussed above, there is at present no method for a large-scale preparation of a stable and sterile liquid thrombin composition. This is due to the lack of stability of thrombin (especially at high temperatures) on the one hand, and to the high viscosity of glycerol, which might make the required filtration step difficult and time-consuming, on the other hand. The surprising finding that liquid thrombin formulations comprising glycerol are both stable at high temperatures and show enhanced ability to reduce bleeding paves the way to a large-scale preparation of sterile liquid thrombin compositions, which includes filtering at elevated temperatures, in which glycerol is less viscous.

The term "preparation" refers to a physiologically acceptable suitable for therapeutic use.

In some aspect, there is provided a sealant formulation comprising thrombin and more than 50% v/v glycerol.

In the context of the present invention, the term "sealant formulation" is to be understood as a single/one component adhesive/glue/hemostat, the formulation having ingredients that upon contact with a tissue and/or blood e.g., in proximity with tissue, react to subsequently form a clot, acting as a tissue adhesive, and thereby prevent, reduce, or stop bleeding, join structures and/or seal physiological leaks, e.g., of cerebrospinal fluids (CSF), lymph, bile, gastrointestinal (GI) content, air leak from lungs etc. In some embodiments, the sealant formulation also comprises therapeutics such that upon natural degradation of the clot formed in the body, the therapeutic is released. The therapeutic may be, without being limited thereto, a drug, such as antibiotics, analgesics, anti-inflammatory drugs, cancer drugs etc., cells including, for example, any type of stem cells e.g., Embryonic Stem (ES) cells, adult stem cells, Pluripotent Stem Cells (iPSCs) etc. from Human or other origin.

It is also possible that the fibrin sealant comprises components which encourage the formation of the clot, such as Ca, Factor VIII, fibronectin, vitronectin, von Willebrand factor (vWF) which can be provided as a separate component or formulated with the liquid components.

At times, the sealant formulation is referred to as a "thrombin-based sealant" and in the context disclosed herein it is to be understood as one forming or meaning a fibrin glue, fibrin sealant, fibrin adhesive, fibrin film, fibrin network, fibrin lattice, fibrin mesh, fibrin greed and fibrin gel.

The disclosed formulations in any aspect thereof, e.g., liquid sealant formulation may be applied onto the tissue using a dispenser that ejects the sealant directly onto the tissue or other substrate or working surface with or without air spray e.g. by dripping. In one embodiment of the invention, the sealant is sprayed at air pressure of 15 PSI. Examples of tissue sealant dispensers are shown in U.S. Pat. Nos. 4,631,055, 4,846,405, 5,116,315, 5,582,596, 5,665, 067, 5,989,215, 6,461,361 and 6,585,696, 6,620,125 and 6,802,822, and PCT Publication No. WO 96/39212, WO 2007/059801, and WO 2010/095128, all of which are incorporated herein by reference.

Embodiments of the liquid thrombin composition and sterile liquid thrombin composition described hereinabove are incorporated to the aspect of the disclosed sealant formulation.

Thus, in some embodiments, the sealant formulation comprises thrombin and more than 50% v/v glycerol. In some embodiments, the sealant formulation comprises about 60 to about 100% v/v glycerol. In some embodiments, the sealant formulation further comprises calcium. In some embodiments, the sealant formulation comprises between about 1 and about 5,000 IU/ml, between about 1 and about 2,000 IU/ml, or between about 100 and about 2,000 IU/ml of thrombin.

Accordingly, in a further aspect, the present invention provides a method for the large-scale production of a sterile liquid thrombin composition comprising more than 50% v/v glycerol, the method comprising the following steps:
 a. preparing a thrombin solution by mixing thrombin with a glycerol solution to obtain a solution having more than 50% v/v glycerol;
 b. heating the obtained thrombin solution to at least 40° C.; and
 c. sterilizing said thrombin solution by passing it through at least one filter having a pore size of 0.22 μm or less, to thereby obtain a liquid sterile thrombin solution comprising more than 50% v/v glycerol.

The term "large-scale" as used herein relates to a process in which at least 1 liter of solution is produced, typically including at least about 400 IU of thrombin.

In some embodiments, the solution is heated to at least 45° C., at least 50° C., at least 55° C., at least 60° C., at least 65° C., at least 70° C., at least 75° C., at least 80° C., at least 85° C., at least 90° C., at least 95° C., or to about 100° C.

In some embodiments, the filter may be a hydrophobic filter.

In some embodiments, more than one filter is used. In some embodiments, at least two filters are used. In some embodiments, at least three filters are used.

Typically, the filtration is sterile filtration, which is defined as a filtering process that does not allow passage to microorganism when tested with at least $10^7$ organisms per $cm^2$ of effective filtration area. Such filters usually have a rated pore size of 0.22 μm or smaller (see 2004 FDA Guidance for Industry Sterile Drug Products Produced by Aseptic Processing—Current Good Manufacturing Practice).

The thrombin solution and/or the elements of the filtration, such as filters, may be temperature controlled prior to and/or during the filtration process. The temperature control may be carried out by various means such as a controlled circulated temperature bath.

For upscaling to larger capacities (such as several kilograms of filtrate), a membrane filter cartridge (such as Supor EX Grade ECV of Pall Corporation®, size of 5" part number AB05UECV2PH4, 10" AB1UECV7PH4, 20" AB2UECV2PH4 or 30" AB3UECV2PH4) may be used. In exemplary embodiments, the Mini Kleenpak™ capsule (surface area 0.023 m²) mentioned in Example 3 below is used since it has a known ratio between the filtrate and the filter surface area that may be duplicated in larger scale by using filter cartridges as aforementioned.

It is appreciated that liquid thrombin formulations including a high glycerol content are also more stable at increased pressures. This feature may come in handy at times of random increased pressure in the system, which normally cause loss of activity of the thrombin, or when there is a need to elevate pressure in order to reduce processing time.

The vessel including the solution which is being filtered may be connected to an energy source that can push the liquid through the filter. The energy source may be compressed air. The vessel may be connected to the energy source through one or more elements that monitor and/or control the energy output. Such element(s) may be a pressure valve and a pressure gauge. The amount of energy permitted to be applied on the thrombin solution may be restricted. The restriction may be of up to 1 bar of pressure on the thrombin solution.

Accordingly, in some embodiments, the filtration is conducted under a pressure of about 1 bar. In some embodiments, the filtration is conducted under a pressure of above 1 bar. In some embodiments, the filtration is conducted under a pressure of above 1.5 bar, above 2 bar, above 2.5 bar, above 3 bar, above 3.5 bar, above 4 bar, above 4.5 bar, or above 5 bar.

In some embodiments, the rate of filtration is less than one hour per 1 kg solution. In some embodiments, the rate of filtration is less than 30 minutes per 1 kg solution. In some embodiments, the rate of filtration is between about 20 and about 30 minutes per 1 kg solution.

Viral safety is a crucial issue when it comes to the risks of human derived products. Since viruses might be carried over in the process of human derived products, these products must go through viral inactivation steps to insure their safety. Traditionally, two viral inactivation methods are independently used to ensure effective reduction of the viral potential load. Some examples for viral inactivation methods used are described below:

Viral inactivation by Nanofiltration—this method may utilize size exclusion to filter out both enveloped and non-enveloped viruses. The filters used are typically has a pore size of less than 70 nm such as Planova 20N, Planova 35N, Viresolve 70, Viresolve 180.

Viral inactivation by Solvent detergent (S/D)—this method may utilize detergents and/or solvents to eliminate lipids found in enveloped or lipid-coated viruses. The detergents and/or solvents being used, such as Triton X-45, Triton X-100 or polysorbate 80, tri(n-butyl) phosphate (TnBP), di- or trialkylphosphates renders the enveloped or lipid-coated viruses inactive. Traditionally, 10-100 mg/ml of solvent detergent is used at a temperature ranging from 2-37° C. with pH level ranging from 5-8 for 30 minutes to 24 hours. After treating the product with S/D, the S/D is usually removed from the product. The combination and concentration of detergents and solvents used is known in the art. For example, a combination of >0.1% TnBP and >0.1% Triton X-100 may be used. In another example, a combination of 1% Triton X-100 and 0.3% TnBP may be used.

Viral inactivation by Heat Inactivation—heat Inactivation, also known as pasteurization, utilizes high temperatures that can harm several types of pathogens including enveloped and non-enveloped viruses. Pasteurization may be achieved by several techniques which usually trades temperature levels to exposer time. For example, the temperature may be 60° C. for a 10-hour duration. In another example Higher Heat Shorter Time technique is used, e.g., at 100° C. for less than a 2 second duration.

However, at least for viral inactivation by heat, such an option has not been available for liquid thrombin due to its lack of stability. Nevertheless, in view of the findings described in the present disclosure, the disclosed liquid thrombin composition containing a high content of glycerol can go through heat-inactivation.

Accordingly, in some embodiment, the method for the large-scale production of a sterile liquid thrombin composition comprising more than 50% v/v glycerol of the invention additionally comprises a step of viral inactivation by heat inactivation.

In some embodiments, the heat inactivation may be carried out at about 60 to 100° C. In some embodiments, the heat inactivation may be carried out at about 60° C. for about 10 hours. In some embodiments, the heat inactivation may be carried out at about 100° C. for less than 2 seconds.

In a further aspect, the present invention provides a sterile liquid thrombin composition comprising more than 50% v/v glycerol obtained by the methods described above.

In yet another aspect, the present invention provides a sterile liquid thrombin composition comprising more than 50% v/v glycerol.

The liquid thrombin composition of the invention may be used as a stand-alone for reducing or stopping bleeding. It may also be used as part of kits to replace frozen or powdered thrombin, or in addition to other hemostatic agents.

In another aspect of the present invention, there is provided a method of treating a wound comprising the step of applying (e.g., contacting) the liquid composition in any aspect and embodiment thereof onto and/or into the wound of a subject in a need thereof.

By "treating a wound" it is further meant to encompass reducing blood loss at a bleeding site of a tissue, e.g., in a patient undergoing surgery.

Accordingly, in some embodiments, the method is for reducing blood loss at a bleeding site of a tissue, e.g., in a patient undergoing surgery, comprising contacting the disclosed composition or formulation in an embodiment thereof with the bleeding site.

In some embodiments, the composition or formulation used for reducing blood loss at a bleeding site of a tissue comprises thrombin and at least 50% glycerol, e.g., about 60% to about 100%, or about 80% to about 100% v/v glycerol. In some embodiments, the composition or formulation further comprises gelatin and/or water e.g., in a supplementary quantity.

As used herein, the term "subject" shall mean any animal including, without limitation, a human, a mouse, a rat, a rabbit, a non-human primate, or any other mammal. In some embodiments, the subject is human, e.g., a human patient. The subject may be male or female.

It is intended that at least the embodiments relating to % glycerol, calcium and excipients, thrombin source and concentrations, as well as to thrombin stability mentioned above be included in all aspects of this application.

The term "about" as used herein means that values that are 10% above or below the indicated value are also intended to be included. Generally, all values in this application are intended to include the term "about".

The terms "comprises", "comprising", "has", "having", "contain", "containing", and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" in the context of medical treatment includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "bleeding" refers to extravasation of blood from any component of the circulatory system. A "bleeding" thus encompasses unwanted, uncontrolled and often excessive bleeding in connection with surgery, trauma, or other forms of tissue damage, as well as unwanted bleedings in patients having bleeding disorders.

As used herein, the terms "controlling", "preventing", or "reducing", which may be used herein interchangeably in the context of the bleeding, including any grammatical inflection thereof, indicate that the rate of the blood extravagated is essentially nullified or is reduced e.g., by 10%, at least 20%, at least 30%, at least 40%, at least 50%, at least 60%, at least 70%, at least 80%, at least 90%, or even by 100%, of the initial rate of bleeding, compared to situation lacking the contact of the disclosed composition in/on the bleeding site. Methods for determining a level of appearance of bleeding are known in the art.

Further, in some embodiments, the terms "controlling", "preventing" or "reducing", in the context of the bleeding are also meant to encompass at least partially sealing blood vessels at the bleeding site e.g., in soft tissues.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Preparation of various glycerol concentrations: For each glycerol concentration, a volume of DDW was drawn into a 5 ml syringe (Yoel Naim 5 ml syringe lot: 20130815) and added into a vial. A volume of glycerol (J.T Baker 500 ml anhydrous glycerol batch: 0000136697) was drawn into a 5 ml syringe and added into the same vial. Each vial containing DDW and/or glycerol was then mixed with a vortex (Scientific industries, Vortex-genie 2 model G560E. speed set 5) for 30 seconds at ambient temperature.

Thrombin reconstitution: For each glycerol concentration 2 ml of liquid containing the different glycerol concentrations was drawn into a 5 ml syringe. The 2 ml of liquid was injected into the Lyophilized Thrombin vials containing about 2000 IU and placed on a roller (Stuart, roller mixer model SRT6) for 24-72 hours (h) for reconstitution at ambient temperature.

Briefly, a thrombin standard curve was created between 4-10 International Units (IU)/ml. 40 ml of thrombin or of a diluted sample were then added to 160 ml of a 0.1% fibrinogen solution in a test cuvette. The time to clot was assayed in an automated clotting machine (Stat4, Stago Diagnostica). The machine generates an oscillating electromagnetic field which moves a small metal ball inside the cuvette. Clotting is determined to have occurred when the ball movement is detected to have stopped. Thrombin concentration in test samples is extrapolated from the clotting times against the standard curve.

Example 1: Liquid Thrombin Stability 24 h stability at 50° C.: Several glycerol concentrations were prepared as described above according to Table 1 below presenting preparation of thrombin solutions with various glycerol concentrations.

TABLE 1

| Glycerol % ((by solvent volume (v/v)) | Glycerol amount | DDW amount | Total amount |
|---|---|---|---|
| 0% | 0 ml | 5 ml | 5 ml |
| 50% | 2.5 ml | 2.5 ml | 5 ml |
| 60% | 3 ml | 2 ml | 5 ml |
| 80% | 4 ml | 1 ml | 5 ml |

Thrombin was reconstituted as described above, and 300 µl samples were taken using a 1 ml syringe (Terumo 1 ml syringe lot: 1001015) into Eppendorf tubes (Sarstedt, 1.5 micro tubes 72.690.001) and frozen (−20° C.) for future analysis as time point 0 (0 hours). The vials containing the rest of the reconstituted Thrombin were placed in an oven (venticell 222, SN: B020251) as needed for the indicated temperature e.g., 50° C., for the indicated time (e.g., 24 hours). At each of the timepoints which were: 1, 4.5, 8 and 24 hours; 300 µl samples were taken using a 1 ml syringe into Eppendorf tubes and frozen for future analysis for the respective time point. Thrombin activity in the test samples was evaluated based on a standard curve, as described above.

The mean results of 4 repetitions of thrombin activity for different glycerol concentration in the 24 h stability study at 50° C. are presented in FIG. 1. As shown in FIG. 1, the activity of thrombin was fully maintained for 25 hours at 50° C., at glycerol concentrations of 50%, 60%, and 80%.

Long Term Stability: The effect of various glycerol concentrations on thrombin activity at various temperatures (° C.) was further testes. Thrombin was suspended in several different concentrations of glycerol in DDW and placed at 25° C. for 6 months and at 4° C. for 12 months, FIG. 2A presents the activity measured at 3 and 6 months at 25° C. FIG. 2B presents the activity measured at 12 months at 4° C. The results demonstrated the long-term stability of the tested glycerol samples, as about 90% to about 100% of the activity was maintained, for each of the indicated time.

Example 2: Liquid Thrombin 2 Minutes Stability at 100° C.

Several glycerol concentrations were prepared as described above according to Table 1 above (50%, 60%, and 80%).

Thrombin was reconstituted as described above, and 300 µl samples were taken using a 1 ml syringe (Terumo 1 ml syringe lot: 1001015) into Eppendorf tubes (Sarstedt, 1.5 micro tubes 72.690.001) for future analysis as time point 0 (0 minutes). The vials containing the rest of the reconstituted Thrombin were placed in an oven (venticell 222, SN: B020251) set for 100° C. for 2 minutes. After 2 minutes, 300 μl samples were taken from each concentration using a 1 ml syringe into Eppendorf tubes. Thrombin activity in the test samples was evaluated based on a standard curve, as described above, and normalized by the result for 0% glycerol at time point 0.

The mean results of 2 repetitions of thrombin activity for different glycerol concentration in the 2 minutes stability study at 100° C. are presented in FIG. 3. As can be seen from FIG. 3, after 2 minutes at 100° C., less than 75% of the thrombin activity was maintained with 50% glycerol, while in solutions of 60% and 80% glycerol, 90% of thrombin activity was maintained.

Example 3: Filtration Rate of Anhydrous Glycerol at Various Temperatures

In order to produce a sterile liquid using filtration, the liquid must pass through a filter with a pore size equal or below 0.22 μM (2004 FDA Guidance for Industry Sterile Drug Products Produced by Aseptic Processing—Current Good Manufacturing Practice). However, it is known that viscus liquids such as glycerol are difficult to pass through such a filter, which results in a very long procedure, making it ineffective at best. Accordingly, the inventors tested whether elevating the temperature of filtration can make the glycerol less viscous and filtration more effective. However, this can only be carried out if thrombin activity is not affected in the process. As shown above in Example 1, the inventors have now established that thrombin in above 50% glycerol is stable at 50° C. for 24 hours. Additionally, as shown in Example 2, the inventors have also established that thrombin in a solution of more than 50% glycerol is stable for 2 minutes at 100° C. As a result, higher temperature may also be used for the filtration process. In this Example, the inventors examined the effect of temperature on the filtration rate of glycerol.

In exemplary procedures, Glycerol (J.T Baker anhydrous glycerol batch: 0000136697) was placed in a pressure vessel (Sartorius Stedim model 17530) and filtered through a 0.2 μM Mini Kleenpak™ capsule filter (PALL Corporation® REF KA02ECV2FT, lot IB2616) using silicone tubing and a compressed air (CA) system connected to a pressure gauge (up to 1 bar) to maintain a pressure of 0.9-1 bar during the process. The pressure vessel with the glycerol and the filter were incubated for 45 minutes prior and during the filtration process inside a controlled circulated temperature bath. In order to evaluate the effect of temperature on the filtration rate, the controlled circulated temperature bath was set to one of three different temperatures, one for each test. The examined temperatures were: 25° C., 40° C., and 50° C.

The filtration rate was measured by weighing the filtrate over time. The results are shown in in Table 2 below demonstrating the effect of filtration temperature on filtration rate.

TABLE 2

| Filtration Temperature (° C.) | Flow rate (kg/hr) |
| --- | --- |
| 25 | 0.42 |
| 40 | 1.02 |
| 50 | 2.22 |

As can be seen from Table 2, the filtration flow rate of glycerol at 25° C. was relatively low, i.e. below 0.5 kg per hour, making it ineffective. However, the filtration flow rate of glycerol at 40° C. and 50° C. was about 2.5-fold and about 5-fold faster, respectively, compared to the process at room temperature, making the process much more effective when conducted at high temperatures. Accordingly, filtration of approximately 1 kg glycerol, which is required for a large-scale preparation, may be achieved in under half an hour at 50° C., compared to approximately 2.5 hours at 25° C.

Example 4: Large Scale Preparation of a Stable Sterile Liquid Thrombin Solution

Based on the combined findings in Examples 1 and 2, showing stability of thrombin at high temperatures, and Example 3, which shows a higher filtration rate of glycerol at elevated temperatures, a liquid thrombin solution comprising more than 50% glycerol could be sterile filtered by elevating the solution temperature and passing it through a filter with pore size of 0.22 μM or less.

In exemplary procedures, thrombin is mixed with glycerol (J.T Baker anhydrous glycerol) and DDW to yield a final volume of 2 liters thrombin solution containing 1000 IU/ml of thrombin in 80% glycerol v/v. The thrombin solution is placed within a Sartorius Stedim model 17530, which is connected to a 0.2 μM Mini Kleenpak™ capsule filter (PALL Corporation® REF KA02ECV2FT, lot IB2616) and a compressed air (CA) system through a pressure gauge and valve. The pressure vessel containing the thrombin solution and the filtering elements are placed within a controlled circulated temperature bath which is set to 50° C. After the thrombin solution and the filtering elements reach 50° C., the pressure is adjusted to 0.9-1 bar by controlling the compressed air flow by the pressure valve and the pressure gauge. A flow rate of over 0.5 kg per hour is expected, resulting in a 1 kg of filtrate, sterile thrombin solution, in less than 2 hours. In fact, based on the experiments in Example 3, a flow rate of approximately 2 kg per hour may be expected, resulting in a 1 kg of filtrate, sterile thrombin solution, in less than half an hour. It is appreciated that elevating the temperature more is expected to result in an even higher rate of filtration.

Example 5: Liquid Thrombin Combined with Gelatin In Vivo Testing

Several glycerol concentrations were prepared as described above according to Table 3, similarly to that shown in Table 1:

TABLE 3

| Glycerol concentrations (by solvent volume) | Glycerol amount | DDW amount | Total amount |
| --- | --- | --- | --- |
| 50% | 2.5 ml | 2.5 ml | 5 ml |
| 60% | 3 ml | 2 ml | 5 ml |
| 100% | 5 ml | 0 ml | 5 ml |

For each glycerol concentration, 8 ml of gelatin paste (from Surgiflo® kit) was prepared with 1,600-2,400 IU of thrombin reconstituted with 2 ml of the various glycerol concentrations were used (instead of the thrombin reconstituted with water according to the kit). All the hemostatic compositions tested comprised: thrombin, gelatin, and glycerol, wherein the glycerol was at a concentration of above 30% of the solids by weight.

Each prepared syringe was labeled with the glycerol concentration used for the thrombin reconstitution. Thrombin activity was tested using in vivo porcine punch biopsy model as described below.

The animal Procedure used was similar to the procedure previously reported in MacDonald et al. 2017, Medical Devices: Evidence and Research 10: 273-279, with the following modifications:

- a disposable biopsy punch of 8 mm with a stop set to 4 mm was used;
- a tamponade was applied for 10 seconds after the test article application and the presence of free-flowing blood was monitored for 2 minutes; and
- the number of tamponades required to achieve no free-flowing blood was noted.

Briefly, a ventral midline abdominal incision was performed, and the cranial portion of the midline incision was extended to improve exposure of the liver. The liver was positioned as necessary to maximize testing surface availability. The abdominal organs were kept moist with saline and saline-soaked laparotomy sponges throughout the procedure. The liver parenchymal defects were created on the diaphragmatic surface of accessible areas of the left, right, and quadrate lobes using a disposable 8 mm biopsy punch with a depth stop set to 4 mm. The core portion of the biopsy was grasped and sharply dissected free from the underlying surface causing mild to moderate hemorrhage.

The defect site was allowed to bleed for several seconds prior to product application to allow for characterization of the resulting hemorrhage. Bleeding at each defect site was classified at a range from 0-5 at the time of wound creation and prior to treatment. Defects classified as 1 or less where excluded and no testing was conducted on them. The trial site was blotted with gauze and then one of the test articles was applied. For the purposes of this study, effective hemostasis was defined as the cessation of free flow bleeding. Pinpoint or petechial bleeding that had appeared but had not grown was not considered to be free flow bleeding. The test article was dispensed onto the defect (bleeding site) by the Surgiflo® applicator. Initial tamponade was applied for approximately 10 seconds using digital pressure on a gauze. Following the initial 10 seconds of tamponade, the dressing was removed. If hemostasis was not achieved after 120 seconds, tamponade was reapplied and maintained for an additional 10 seconds followed by another observation period. This process was repeated until effective hemostasis was achieved, and the number of required tamponades was recorded.

The mean of 5 repetitions of efficacy results of thrombin reconstituted with glycerol combined with gelatin in the porcine punch biopsy in vivo model are presented in FIG. 4.

As can be seen from FIG. 4, the % glycerol in the thrombin solution directly affected the results, with 50% glycerol resulting on average in about 2.8 tamponade repetitions, 60% glycerol resulting in an average of about 1.8 tamponade repetitions, and 100% glycerol resulting in less than 1.5 tamponade repetitions on average.

For comparison, it was previously reported that Surgicel® (Absorbable Hemostatic Powder) was superior to AR (Arista™ AH Absorbable Hemostatic Particles) and PC (PerClot® Polysaccharide Hemostatic System) in a similar model (MacDonald et al. 2017, mentioned above). In that model, both Arista™ and PerClot® had a time-to-hemostasis of equal or over 4.75 minutes. Since each observation after each tamponade is of maximum 2 minutes, the results of Arista and PerClot® are equivalent to equal or over 2.3 tamponades.

Therefore, the results of this study demonstrate the increased efficacy for thrombin reconstituted in 60% glycerol or above compared to existing products of thrombin reconstituted in water without glycerol.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A hemostatic kit comprising:
   a. a container containing a liquid composition of a large-scale and storage-stable sterile preparation comprising thrombin and more than about 60% v/v glycerol; and
   b. a container containing gelatin;
   wherein the storage-stable sterile preparation is characterized in that the thrombin in the liquid composition retains at least 90% of its original activity after about 2 minutes at a temperature of about 100° C.

2. The hemostatic kit according to claim 1, wherein the liquid composition comprises about 80% to about 100% v/v glycerol.

3. The hemostatic kit according to claim 1, wherein the kit further comprises calcium.

4. The hemostatic kit according to claim 1, wherein the liquid composition further comprises one or more excipients selected from the group consisting of sodium chloride, mannitol, albumin, and sodium acetate.

5. The hemostatic kit according to claim 1, wherein the liquid composition comprises between about 100 and about 2,000 IU/ml of thrombin.

* * * * *